(12) United States Patent
Takeshima et al.

(10) Patent No.: US 11,129,542 B2
(45) Date of Patent: Sep. 28, 2021

(54) MAGNETIC RESONANCE IMAGING APPARATUS

(71) Applicant: Canon Medical Systems Corporation, Otawara (JP)

(72) Inventors: Hidenori Takeshima, Kawasaki (JP); Hitoshi Kanazawa, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 6 days.

(21) Appl. No.: 16/550,876

(22) Filed: Aug. 26, 2019

(65) Prior Publication Data
US 2020/0069214 A1    Mar. 5, 2020

(30) Foreign Application Priority Data

Sep. 5, 2018  (JP) .............................. JP2018-166101

(51) Int. Cl.
| | |
|---|---|
| *G01V 3/00* | (2006.01) |
| *A61B 5/055* | (2006.01) |
| *G01R 33/385* | (2006.01) |
| *G01R 33/483* | (2006.01) |
| *G01R 33/561* | (2006.01) |
| *G01R 33/56* | (2006.01) |

(52) U.S. Cl.
CPC ............ *A61B 5/055* (2013.01); *G01R 33/385* (2013.01); *G01R 33/4833* (2013.01); *G01R 33/5608* (2013.01); *G01R 33/5611* (2013.01); *G06T 2207/10088* (2013.01)

(58) Field of Classification Search
CPC .............. G01R 33/3415; G01R 33/543; G01R 33/5659; G01R 33/36; A61B 5/055
USPC ......................................................... 324/307
See application file for complete search history.

(56) References Cited

U.S. PATENT DOCUMENTS

| | | | | |
|---|---|---|---|---|
| 6,396,856 B1* | 5/2002 | Sucha | ................... | H01S 3/2383 372/25 |
| 8,928,318 B2 | 1/2015 | Nitta et al. | | |
| 2008/0119721 A1* | 5/2008 | Kimura | ................... | A61B 5/055 600/410 |

(Continued)

FOREIGN PATENT DOCUMENTS

| | | |
|---|---|---|
| JP | 2002-360532 A | 12/2002 |
| JP | 2012-110689 A | 6/2012 |
| JP | 2015-33577 A | 2/2015 |

OTHER PUBLICATIONS

JP-2002360532-A, Yamazaki, Aki JP Dec. 17, 2002.*

(Continued)

*Primary Examiner* — Walter L Lindsay, Jr.
*Assistant Examiner* — Frederick Wenderoth
(74) *Attorney, Agent, or Firm* — Oblon, McClelland, Maier & Neustadt, L.L.P.

(57) ABSTRACT

According to one embodiment, a magnetic resonance imaging apparatus includes processing circuitry. The processing circuitry collects magnetic resonance data in accordance with a pulse sequence. The processing circuitry determines image quality based on the magnetic resonance data. The processing circuitry selects a re-collection pulse sequence when it is determined that the image quality does not satisfy criteria, the re-collection pulse sequence having at least one of a type of sequence or an imaging condition differing from that of the pulse sequence.

18 Claims, 10 Drawing Sheets

(56) References Cited

U.S. PATENT DOCUMENTS

| | | | | |
|---|---|---|---|---|
| 2013/0237806 A1* | 9/2013 | Blumhagen | .......... | A61B 6/5247 |
| | | | | 600/411 |
| 2014/0107467 A1* | 4/2014 | Felmlee | ............... | A61B 5/0035 |
| | | | | 600/411 |
| 2014/0354282 A1* | 12/2014 | Kusik | .................. | G01R 33/283 |
| | | | | 324/322 |
| 2015/0238149 A1 | 8/2015 | Nitta et al. | | |
| 2015/0253199 A1* | 9/2015 | Sartorius | ............... | H01S 3/0014 |
| | | | | 250/341.3 |
| 2016/0216350 A1* | 7/2016 | Feiweier | ................ | A61B 5/055 |

OTHER PUBLICATIONS

"HeartVista Announces One Click Autonomous MRI Solution", Imaging Technology News, Magnetic Resonance Imaging (MRI), Nov. 25, 2018, 2 pages.

* cited by examiner

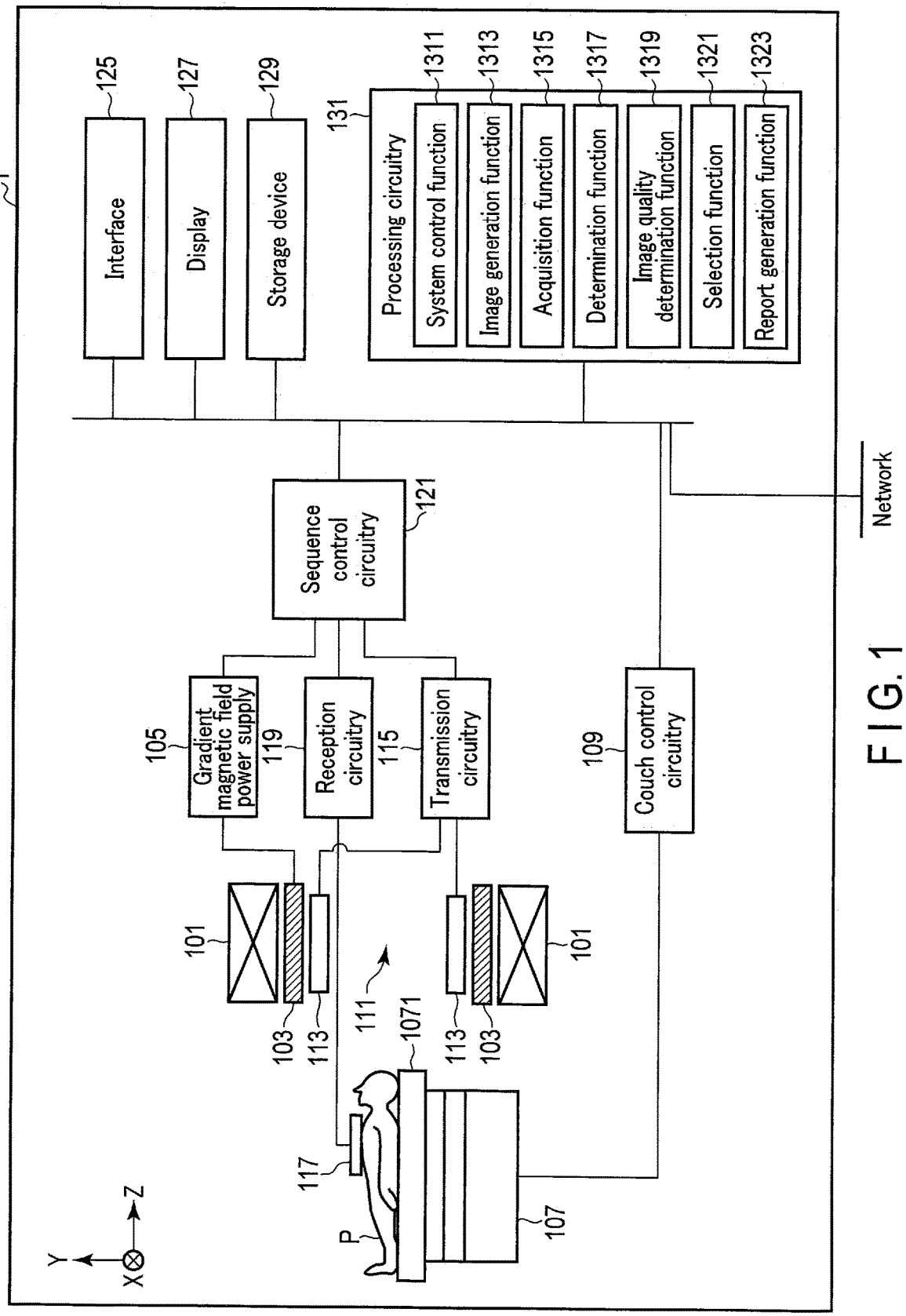
F I G. 1

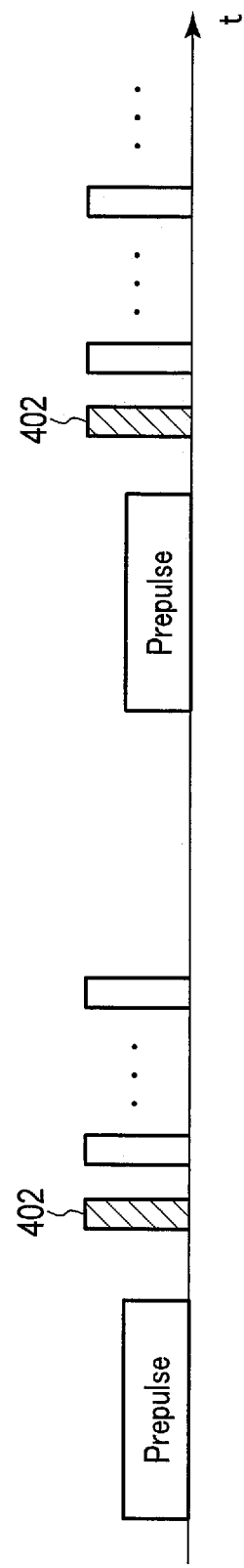

| Causes | Sequence selection orders |
|---|---|
| Motion artifact (voluntary motion, failure in holding of breath) | FSE ↓ GRASE ↓ FSE-PROPELLER |
| Banding artifact (magnetic field disturbance) | SSFP ↓ Center frequency-changed SSFP ↓ FastFE |
| Predicted time exceeded (Larger FOV necessary, failure in gating) | Parallel Imaging (SENSE/GRAPPA) ↓ Parallel Imaging+Compressed sensing |
| Target off-centered | Move couch ↓ Enlarge FOV |

F I G. 6

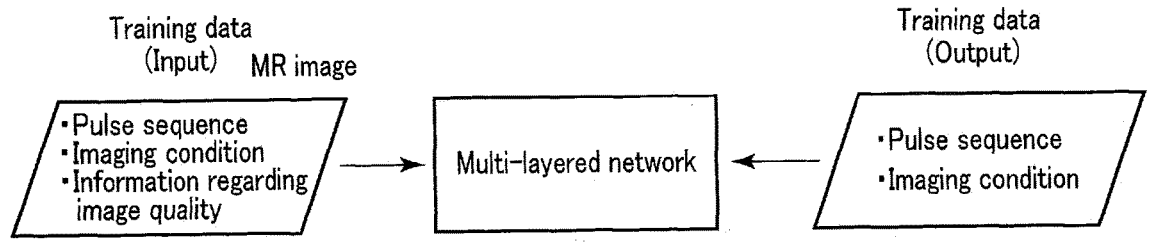
FIG. 8
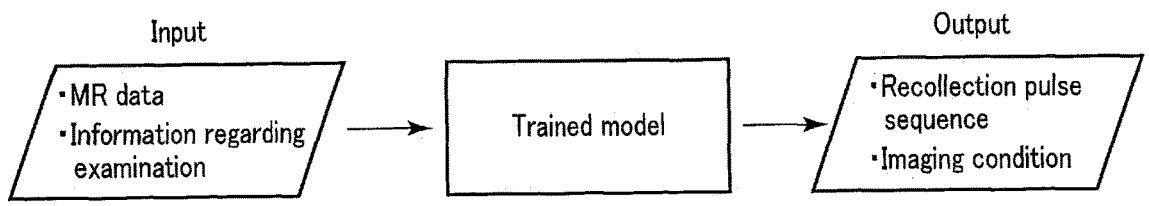
FIG. 9
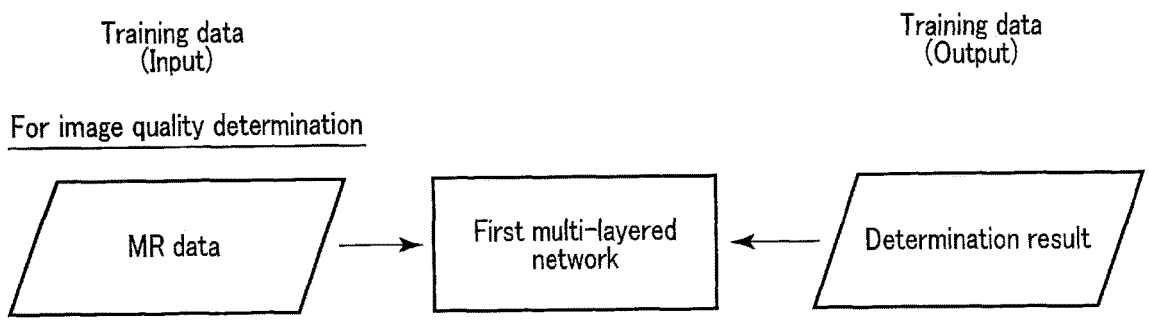
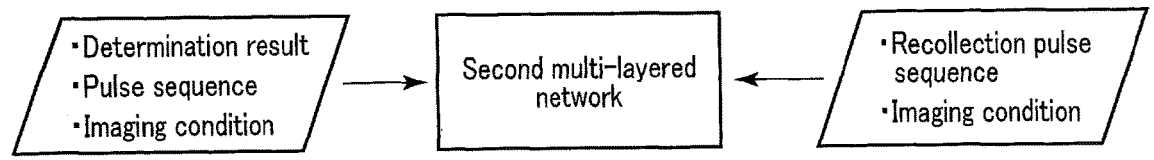
FIG. 10

MAGNETIC RESONANCE IMAGING APPARATUS

CROSS-REFERENCE TO RELATED APPLICATIONS

This application is based upon and claims the benefit of priority from the prior Japanese Patent Application No. 2018-166101, filed Sep. 5, 2018, the entire contents of which are incorporated herein by reference.

FIELD

Embodiments described herein relate generally to a magnetic resonance imaging apparatus.

BACKGROUND

If imaging fails during the main imaging of a subject, it is necessary to reattempt imaging upon a technician's judgment. A simple reattempt of imaging with the same sequence is one technique that may be followed. However, in a case where a reattempt at imaging is required as a result of a subject's body motion caused by his or her breathing during initial imaging, a mere attempt of the same sequence within the same breath-hold period is also likely to deliver failure. Consequently, a reattempt of imaging that requires a technician's judgment eventually becomes necessary. However, this leads to the possible emergence of a subsequent problem, namely that the results of imaging may vary greatly depending on technician's level of skill.

BRIEF DESCRIPTION OF THE DRAWINGS

FIG. 1 is a block diagram showing a configuration of a magnetic resonance imaging apparatus according to an embodiment.

FIG. 4B is a drawing showing a second example of collection of a calibration signal used in image quality determination processing.

FIG. 6 is a drawing showing re-collection pulse sequence selection processing.

FIG. 8 is a conceptual drawing of machine learning of a model if the process according to the embodiment is realized by a single trained model.

FIG. 9 is a conceptual drawing of a use of the trained model according to FIG. 8.

FIG. 10 is a conceptual drawing of machine learning of a model if the process according to the embodiment is realized by separate trained models.

DETAILED DESCRIPTION

Figure 2:
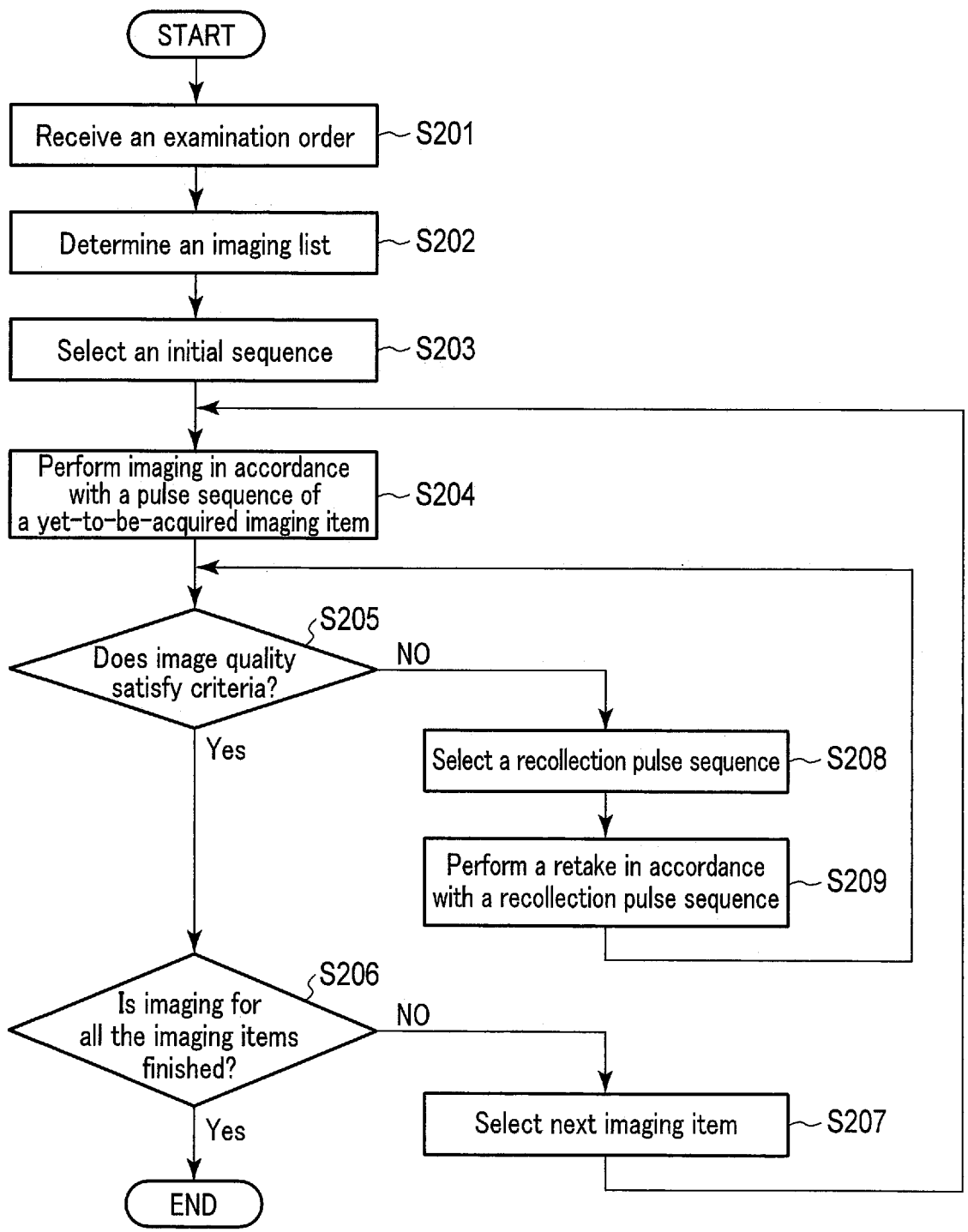
FIG. 2 is a flow chart showing an example of an operation of the magnetic resonance imaging apparatus according to the embodiment.

In general, according to one embodiment, a magnetic resonance imaging apparatus includes processing circuitry. The processing circuitry collects magnetic resonance data in accordance with a pulse sequence. The processing circuitry determines image quality based on the magnetic resonance data. The processing circuitry selects a re-collection pulse sequence when it is determined that the image quality does not satisfy criteria, the re-collection pulse sequence having at least one of a type of sequence or an imaging condition differing from that of the pulse sequence.

A magnetic resonance imaging (MRI) apparatus according to the present embodiment will be described with reference to the accompanying drawings. In the embodiments described below, elements assigned with the same reference symbols perform the same operations, and redundant descriptions thereof will be omitted as appropriate. Hereinafter, one embodiment will be described with reference to the drawings.

The general configuration of an MRI apparatus 1 in the present embodiment will be described with reference to FIG. 1. FIG. 1 is a diagram showing a configuration of the MRI apparatus 1 in the present embodiment. As shown in FIG. 1, the MRI apparatus 1 includes a static magnetic field magnet 101, a gradient coil 103, a gradient magnetic field power supply 105, a couch 107, couch control circuitry 109, a transmitter coil 113, transmission circuitry 115, a receiver coil 117, reception circuitry 119, sequence control circuitry 121, a bus 123, an interface 125, a display 127, a storage apparatus 129, and processing circuitry 131. The MRI apparatus 1 may have a hollow, cylindrical-shaped shim coil provided between the static magnetic field magnet 101 and the gradient coil 103.

The static magnetic field magnet 101 is a magnet formed in a hollow, approximately cylindrical shape. The static magnetic field magnet 101 is not necessarily in an approximately cylindrical shape; it may be formed in an open shape. The static magnetic field magnet 101 generates a uniform static magnetic field in the inner space. For example, a superconducting magnet or the like is used as the static magnetic field magnet 101.

The gradient coil 103 is a hollow cylindrical coil. The gradient coil 103 is provided inside the static magnetic field magnet 101. The gradient coil 103 is formed by combining three coils respectively corresponding to the X-, Y-, and Z-axes which are orthogonal to each other. The Z-axis direction is defined as the same as the orientation of the static magnetic field. In addition, the Y-axis direction is a vertical direction, and the X-axis direction is a direction perpendicular to each of the Z-axis and the Y-axis. The three coils of the gradient coil 103 individually receive an electric current from the gradient magnetic field power supply 105 and respectively generate gradient magnetic fields in which magnetic field intensity changes along each of the X-, Y-, and Z-axes.

The gradient magnetic fields along each of the X-, Y-, and Z-axes generated by the gradient coil 103 respectively form, for example, a gradient magnetic field for frequency encoding (readout gradient field), a gradient magnetic field for phase encoding, and a gradient magnetic field for slice selection. The gradient magnetic field for slice selection is used to determine an imaging slice. The gradient magnetic field for phase encoding is used to change the phase of a magnetic resonance (hereinafter referred to as MR) signal in accordance with the spatial position. The gradient magnetic field for frequency encoding is used to change the frequency of an MR signal in accordance with the spatial position.

The gradient magnetic field power supply 105 is a power supply device that supplies an electric current to the gradient coil 103 under the control of the sequence control circuitry 121.

The couch 107 is an apparatus having a couch top 1071 on which a subject P is laid. The couch 107 inserts the couch top 1071 on which the subject P is laid into the bore 111 under the control of the couch control circuitry 109. The couch 107 is installed in, for example, an examination room where the MRI apparatus 1 is installed, in such a manner that the longitudinal axis of the couch 107 is parallel to the center axis of the static magnetic field magnet 101.

The couch control circuitry 109 is circuitry that controls the couch 107 in response to an operator's instruction via the interface 125 to move the couch top 1071 in a longitudinal direction and a vertical direction.

The transmitter coil 113 is an RF coil provided inside the gradient coil 103. The transmitter coil 113 is supplied with the RF pulse from the transmission circuitry 115 and generates a transmit RF wave corresponding to a radio frequency magnetic field. The transmitter coil 113 is a whole body coil (WBC), for example. The WBC coil may be used as a transmitter/receiver coil. A cylindrical RF shield is arranged between the WBC and the gradient coil 103 to magnetically separate these coils.

The transmission circuitry 115 supplies an RF pulse corresponding to a Larmor frequency, etc. to the transmitter coil 113 by the control of the sequence control circuitry 121.

The receiver coil 117 is an RF coil provided inside the gradient coil 103. The receiver coil 117 receives MR signals that are emitted from the subject P, caused by a radio frequency magnetic field. The receiver coil 117 outputs the received MR signals to the reception circuitry 119. The receiver coil 117 is a coil array including, for example, one or more, typically, a plurality of coil elements. The receiver coil 117 is a phased array coil (PAC), for example.

The reception circuitry 119 generates, under the control of the sequence control circuitry 121, a digital MR signal (hereinafter, "MR data"), which is digitized complex number data, based on the MR signal that is output from the receiver coil 117. Specifically, the reception circuitry 119 performs various types of signal processing to the MR signal output from the receiver coil 117, and then performs analog-to-digital (A/D) conversion of data to which the variety of signal processing is performed. The reception circuitry 119 samples the A/D-converted data. The reception circuitry 119 thereby generates MR data. The reception circuitry 119 outputs the generated MR data to the sequence control circuitry 121.

The sequence control circuitry 121 controls the gradient magnetic field power supply 105, the transmission circuitry 115, and the reception circuitry 119 etc. in accordance with an examination protocol that is output from the processing circuitry 131, and performs imaging on the subject P. An examination protocol has different pulse sequences in accordance with a type of examination. The examination protocol defines the magnitude of the current supplied from the gradient magnetic field power supply 105 to the gradient coil 103, timing of the supply of the current from the gradient magnetic field power supply 105 to the gradient coil 103, the magnitude of the RF pulse supplied from the transmission circuitry 115 to the transmitter coil 113, timing of the supply of the RF pulse from the transmission circuitry 115 to the transmitter coil 113, and timing of reception of the MR signal at the receiver coil 117, etc. The sequence control circuitry 121 outputs the MR data received from the reception circuitry 119 to the processing circuitry 131.

The bus 123 is a transmission path for transmitting data between the interface 125, the display 127, the storage 129, and the processing circuitry 131. The bus 123 may be connected via, for example, a network to various physiological signal measuring devices, an external storage apparatus, and various modalities. For example, an electrocardiograph (not shown) is connected to the bus as a physiological signal measuring device.

The interface 125 has circuitry for receiving various types of instructions and information input from an operator. The interface 125 includes a circuit relating to, for example, a pointing device such as a mouse, or an input device such as a keyboard. The circuit included in the interface 125 is not limited to a circuit relating to a physical operational component, such as a mouse or a keyboard. For example, the interface 125 may include an electrical signal processing circuit which receives an electrical signal corresponding to an input operation from an external input device provided separately from the present MRI apparatus 1 and outputs the received electrical signal to various circuits.

The display 127 displays, for example, various magnetic resonance (MR) images generated by an image generation function 1313, and various types of information relating to imaging and image processing, under the control of a system control function 1311 in the processing circuitry 131. The display 127 is, for example, a CRT display, a liquid crystal display, an organic EL display, an LED display, a plasma display, or any other display or a monitor known in this technical field.

The storage apparatus 129 stores, for example, MR data filled in k-space by the image generation function 1313, and image data generated by the image generation function 1313. The storage apparatus 129 stores various types of examination protocols, conditions for imaging etc., including a plurality of imaging parameters that define examination protocols. The storage apparatus 129 stores programs corresponding to various functions executed by the processing circuitry 131. The storage apparatus 129 is, for example, a semiconductor memory element, such as a random access memory (RAM) and a flash memory, a hard disk drive, a solid state drive, or an optical disk, etc. The storage apparatus 129 may also be, for example, a drive that performs reading and writing various kinds of information on a portable storage medium such as a CD-ROM drive, a DVD drive, or a flash memory.

The processing circuitry 131 has, as hardware resources, a processor and a memory such as a read-only memory (ROM) and a RAM (not shown), and collectively controls the present MRI apparatus 1. The processing circuitry 131 includes a system control function 1311, an image generation function 1313, an acquisition function 1315, a determination function 1317, an image quality function 1319, a selection function 1321, and a report generation function 1323. These various functions are stored in the storage device 129 in a form of program executable by a computer. The processing circuitry 131 is a processor which reads a program corresponding to each function from the memory apparatus 129 and executes the program to realize the function corresponding to the program. In other words, the processing circuitry 131, in a state where each of the programs is read, has a plurality of the functions etc. shown in the processing circuitry 131 of FIG. 1.

FIG. 1 illustrates that the various functions are realized by single processing circuitry 131; however, the processing circuitry 131 may include a plurality of independent processors, and the functions may be realized by each of the processors executing respective programs. In other words, each of the above-mentioned functions may be configured as a program, and executed by a single processing circuit; alternatively, a specific function may be implemented in a dedicated independent program-execution circuit.

The term "processor" used in the above explanation means, for example, circuitry such as a CPU (central processing unit), a GPU (graphics processing unit), an ASIC (application specific integrated circuit), or a programmable logic device (for example, an SPLD (simple programmable logic device), a CPLD (complex programmable logic device), or an FPGA (field programmable gate array)).

The processor reads and executes a program stored in the storage 129 to activate the corresponding function. The programs may be directly integrated in a circuit of the processor, instead of being stored in the storage apparatus 129. In this case, the function is realized by reading and executing the program integrated into the circuitry. Similarly, each of the couch control circuitry 109, the transmission circuitry 115, the reception circuitry 119, and the sequence control circuitry 121, etc. are also configured as an electronic circuit, such as the above processor.

The processing circuitry 131 controls the MRI apparatus 1 by the system control function 1311. Specifically, the processing circuitry 131 reads the system control program stored in the storage apparatus 129, loads it in the memory, and controls each circuitry of the present MRI apparatus 1 in accordance with the loaded system control program. For example, the processing circuitry 131 reads an examination protocol from the storage apparatus 129 by the system control function 1311 based on an imaging condition input by the operator via the interface 125. The processing circuitry 131 may generate the examination protocol based on the imaging condition. The processing circuitry 131 transmits the examination protocol to the sequence control circuitry 121 to control imaging of the subject P.

The processing circuitry 131 fills MR data along a readout direction of k-space in accordance with, for example, an intensity of the readout gradient magnetic field via the image generation function 1313. The processing circuitry 131 generates an MR image by executing a Fourier transform to the MR data filled in k-space. The processing circuitry 131 outputs the generated MR image to the display 127 and the storage apparatus 129.

By executing of the acquisition function 1315, the processing circuitry 131 receives an examination order. The examination order in the present embodiment includes at least an examination item and an examination time. An Examination item includes a body part of a subject P targeted for examination, such as head or abdomen. An examination time is a time window that can be secured in a standard reservation for an examination of a subject P, and a unit for a time window is for example ten minutes, thirty minutes, or one hour.

The processing circuitry 131 determines, through the determination function 1317, an imaging list (may be referred to as "programmable anatomical scan (PAS)") based on the examination order. An imaging list is a list of types of imaging required for an examination of a subject P. The imaging according to the present embodiment includes an image obtained through a contrast enhanced method. Imaging is associated with one or more pulse sequence candidates with which the imaging is achieved. The imaging list will be later described in detail with reference to FIG. 5.

The processing circuitry 131 determines, by executing of the image quality determination function 1319, image quality based on MR data received from the sequence control circuitry 121.

If it is determined that image quality does not satisfy the criteria, the processing circuitry 131 selects, by executing of the selection function 1321, a re-collection pulse sequence in which at least one of a sequence type or an imaging condition differs from that of a pulse sequence.

After performance of the imaging in the imaging list is completed, the processing circuitry 131 generates, by executing of the report generation function 1323, a report regarding an examination result based on an image corresponding to a type of imaging.

the operation of the MRI apparatus 1 according to the present embodiment will be described with reference to the flow chart of FIG. 2.

In step S201, by executing of the acquisition function 1315, the processing circuitry 131 receives an examination order.

In step S202, the processing circuitry 131 determines, by executing of the determination function 1317, an imaging list based on the examination order. In a case where a necessary imaging list is determined from the examination order, the determination can be made in a rule-based manner. For example, a table in which an examination item is associated with one or more generally-assumed imaging items necessary for conducting diagnosis for said examination item is prepared. The table may be stored, for example, either in the storage device 129 or in an external device so as to be referred to by the processing circuitry 131 via a network. The processing circuitry 131 refers to the table by executing of the determination function 1317, and selects an imaging item corresponding to an examination item in the examination order, thereby determining an imaging list.

In step S203, the processing circuitry 131 selects, by executing of the selection function 1321, an initial pulse sequence (may be referred to as "initial sequence") to each imaging item included in the imaging list.

In step S204, the processing circuitry 131 performs, by executing of the system control function 1311, for example, imaging on a subject P, following an initial sequence relating to a-yet-to-be-acquired imaging item in the imaging list. Specifically, in the initial processing in step S204, imaging is performed to obtain MR data in accordance with the initial sequence selected in step S203.

In step S205, as image quality determination processing, the processing circuitry 131 determines, by executing of the image quality determination function 1319, whether or not image quality of MR image based on the MR data obtained in step S204 satisfies criteria. The determination on whether or not image quality satisfies criteria may be made in such a manner that, for example, if there is no artifact in the MR image, the criteria is satisfied and, if artifact is present, the criteria is not satisfied. Furthermore, image quality may be determined in k-space data prior to reconstruction of the MR data; for example, k-space data collected with the use of the Stack-of-Stars method may be reconstructed for one dimension of the stack direction or two dimensions of the radial scan direction, and if there is distortion caused by body motion in a common signal portion, it can be determined that image quality does not satisfy criteria. The determination of whether or not image quality satisfies criteria may be made in such a manner that, for example, if a part of interest is included in the MR image or located approximately at the center thereof, image quality satisfies criteria, and if a part of interest is not included or not located approximately at the center thereof, image quality does not satisfy criteria. To reflect a personal point of view in a determination, if a doctor, etc. inputs, through the interface 125, an instruction indicating that image quality satisfies criteria, it may be determined that image quality satisfies criteria, and if an instruction indicating that image quality does not satisfy criteria is input via the interface 125, it may be determined that image quality does not satisfy criteria.

If it is determined that image quality satisfies criteria, the processing proceeds to step S206, and if it is determined that image quality does not satisfy criteria, the processing proceeds to step S208.

In step S206, the processing circuitry 131, by executing of the system control function 1311, for example, determines whether or not imaging corresponding to all the imaging items included in the imaging list is finished. If imaging for all the imaging items is finished, the imaging is determined as finished; if otherwise, the processing proceeds to step S207.

In step S207, since image quality of an image of the previously-obtained imaging item satisfies criteria, the processing circuitry 131 finishes ongoing imaging corresponding to the imaging item, and selects, via the selection function 1321, the next imaging item from the imaging list. Thereafter, the processing returns to step S204, and the same processing is repeated.

In step S208, since it is determined that image quality does not satisfy criteria in the preceding step S205, the processing circuitry 131 selects, by executing of the selection function 1321, a re-collection pulse sequence from the pulse sequence candidates in the imaging list for the ongoing imaging item. At this time, since obtaining of the imaging items in the list within a permitted examination time is most highly prioritized, if a need of a retake for a certain imaging item arises, a pulse sequence is reselected in consideration of imaging time for the other imaging items after the imaging item for which a retake is determined as necessary.

In other words, if the processing in steps S205, S208, and S209 is repeated, the processing circuitry 131 selects, by executing of the selection function 1321, a new re-collection pulse sequence from the pulse sequence candidates based on imaging time predicted for the imaging items other than the ongoing imaging, and remaining time of the permitted examination time.

In step S209, the processing circuitry 131 performs, by executing of the system control function 1311, a retake in accordance with the re-collection pulse sequence. Thereafter, the processing returns to step S205, and the image quality determination processing is performed. This concludes the operation of the MRI apparatus 1 according to the present embodiment.

After the imaging for all the imaging items is finished, the processing circuitry 131 may generate a report on an examination result by executing of the report generation function 1323. For example, a report is generated from a target imaging item in accordance with a trained model into which a plurality of images relating to the imaging items obtained according to the imaging list are input, and from which a past report based on previous imaging is output. The generated report may be displayed on the display 127, or externally transmitted via a network.

Next, the details of the image quality determination processing by the image quality determination function 1319 will be described.

In the image quality determination processing, image quality may be determined through a conventional image processing on an image (e.g., if artifact exists in an image, it is determined that image quality does not satisfy criteria) based on an MR image obtained by reconstructing collected MR data; however, it may be possible to determine image quality from a calibration signal, without reconstructing MR data.

Specifically, in a pulse sequence, a calibration signal for determining image quality is periodically collected in a readout direction, and image quality is determined based on the calibration signal. In other words, an identical position in k-space is continuously collected in a pulse sequence. For example, a calibration signal is continuously collected for a single row in a readout direction in the same phase encoding on k-space. A Fourier transform is performed on MR data based on the collected calibration signal, and image quality is determined based on an amount of change in the Fourier-transformed signal.

For example, if L1 error or L2 error of a signal vector of the Fourier-transformed signal is equal to or greater than a threshold, it can be determined that distortion occurs in k-space data, and image quality does not satisfy criteria.

A few rows of calibration signals, each having different gradient magnetic fields for phase encoding, may be collected in a readout direction on k-space. Image quality based on an amount of change in the calibration signal may be determined with the use of a sinogram obtained by performing a Fourier transform on the few rows of calibration signal. It may be possible to determine image quality from an amount of change in the calibration signal itself, without performing a Fourier transform on the calibration signals.

Next, the first example of collection of a calibration signal used for image quality determination processing according to the present embodiment will be described with reference to FIG. 3.

Figure 3:
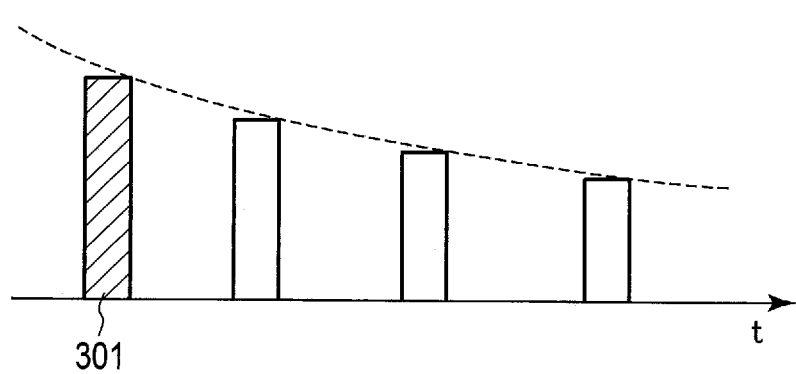
FIG. 3 is a drawing showing a first example of collection of a calibration signal used in image quality determination processing.

FIG. 3 shows the echo signals collected by an FSE (fast spin echo) pulse sequence in a time-series manner.

For example, an initial echo signal 301 (startup echo signal 301—not used for image generation), after an application of an excitation pulse, may be collected as a calibration signal for image quality determination. If it is difficult to determine image quality only with the startup echo signal 301, collection of another echo signal not used for image generation may be added at the end of the collection of the echo signal in a regular FSE pulse sequence, so that said echo signal may be collected as a calibration signal.

Next, the second example of collection of a calibration signal used for the image quality determination processing will be described with reference to FIGS. 4A and 4B.

Figure 4A:
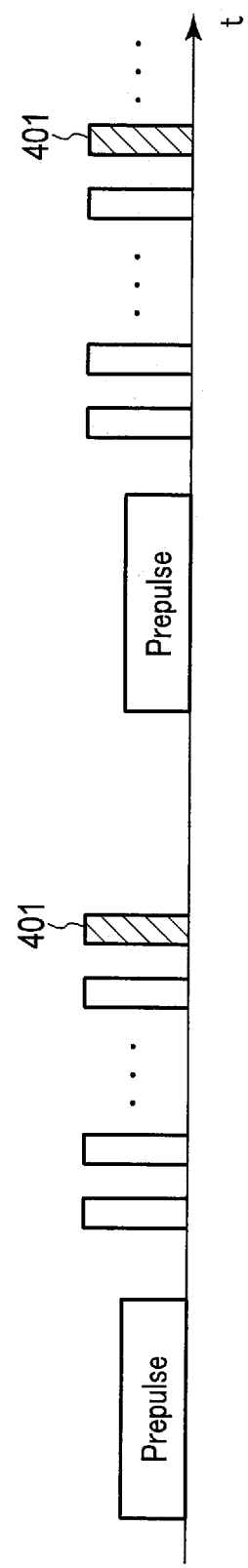
FIG. 4A is a drawing showing a second example of collection of a calibration signal used in image quality determination processing.

FIG. 4A shows the echo signals collected by a Fast GRE (gradient echo) pulse sequence in a time-series manner. The echo signal is collected after a prepulse is applied, with a gradient magnetic field being altered.

In the collection of echo signal, an echo signal 401 not used for the image generation may be collected as a calibration signal after a last echo signal used for the image generation. In other words, an echo signal immediately before the application of a prepulse may be collected as a calibration signal.

Alternatively, as shown in FIG. 4B, if the last echo signal 402 immediately after the application of a prepulse is not used for the image generation, this echo signal 402 may be collected as a calibration signal.

Although not shown, it multi-segment collection is performed to use EPI as a sequence, a calibration signal may be collected for each shot.

Next, an example of the imaging list will be described with reference to FIG. 5.

Figure 5:
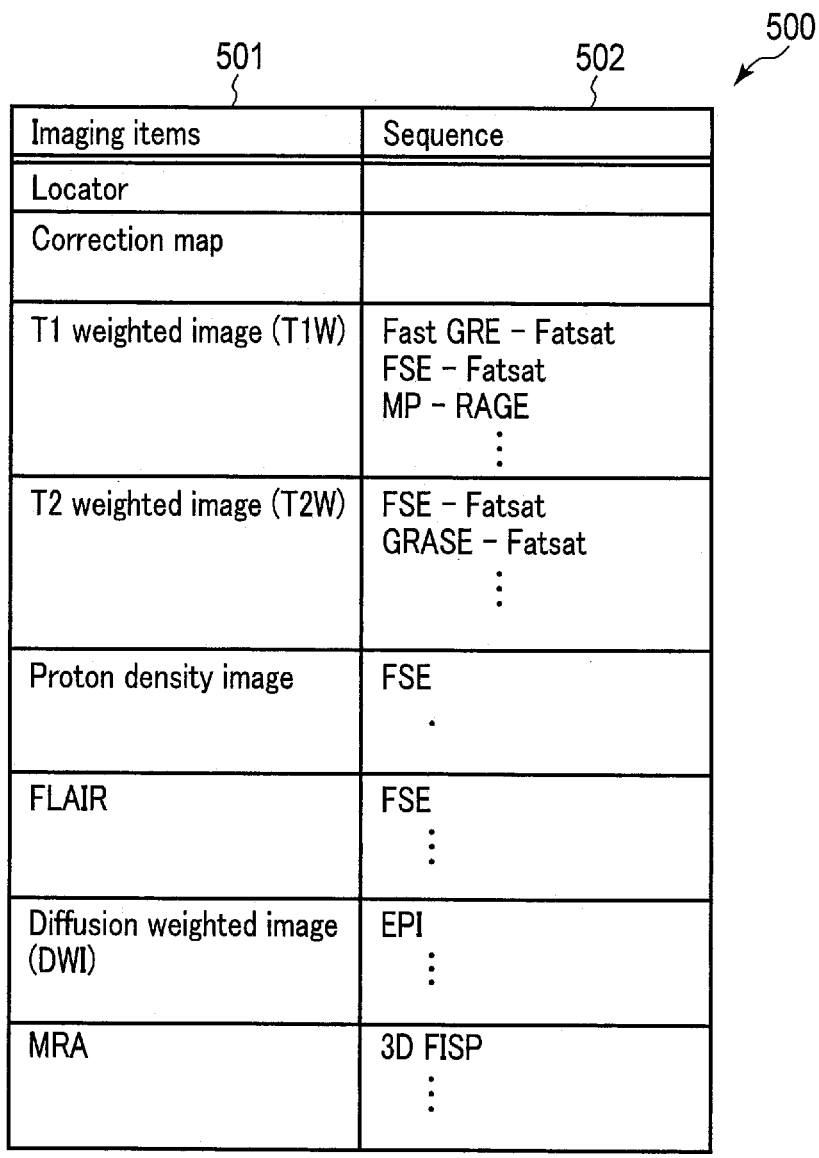
FIG. 5 illustrates an example of an imaging list according to the embodiment.

In the table of the imaging list 500 shown in FIG. 5, each of the multiple types of imaging 501 determined based on an examination order is associated with a plurality of sequence candidates 502. Suppose the imaging items 501 are listed basically in the order of imaging in the imaging list 500. The imaging items 501 shown in FIG. 5 are concepts including a contrast-enhanced method, such as T1 weighted, T2 weighted, proton density enhanced, DWI, MRA, and the like. The imaging items 501 include a contrast-enhanced method for images not directly used for diagnosis, such as a locator and a correction map, etc.

For example, if the imaging item 501 is a T1 weighted image, a plurality of sequences, such as Fast GRE-Fatsat, FSE-Fatsat, MP-RAGE (magnetization prepared rapid acquisition GRE), are associated with the imaging item 501 as the sequence candidates 502 for obtaining an T1 weighted image. If the imaging item 501 is T2 weighted, a plurality of sequences, such as FSE-Fatsat, GRASE (gradient and spin echo)-Fatsat, are associated with the imaging item 501 as the sequence candidates 502 for obtaining a T2-weighted image.

The sequences may be prioritized in the order of levels of image quality; however, the order of priority may be given by different criteria, such as the order of fat suppression effects. The imaging list 500 may be generated for each body part targeted for imaging, and may be stored in the storage device 129 in advance.

Through the obtainment of a locator, a field of view, presence/absence of couch motion, and the time of subject P's respiration are determined. After obtainment of the locator, an imaging condition of the next imaging item 501 in the imaging list is selected, and imaging time is estimated from this point until the imaging corresponding to the next imaging item following the locator is finished.

According to the imaging list 500 of FIG. 5, a correction map is obtained after the obtainment of the locator; however, it may be possible to retake a correction map after the imaging for all the imaging items is finished. For example, if a failure of fat suppression is detected during the obtainment of T1 weighted imaging among the other imaging items 501, a correction map may be retaken. In this case, the processing circuitry may add, by executing of the determination function 1317, a correction map as an imaging item and a corresponding pulse sequence to the imaging list for a retake of a correction map. It is also possible to include a spare imaging item for retaking a correction map in the imaging list 500, and the processing circuitry 131 may select, through the selection function 1321, a pulse sequence for retaking a correction map as a re-collection pulse sequence as necessary.

Next, the selection processing of a re-collection pulse sequence by the selection function 1321 will be described with reference to FIG. 6.

The table 600 shown in FIG. 6 shows a correspondence between causes 601 of retake, and sequence selection orders 602 to remedy the causes 601. A pulse sequence that appears first in each sequence selection order 602 is an initial sequence.

For example, when the cause 601 of a retake is motion artifact due to failure in subject P's holding his or her breath, the processing circuitry 131 selects, via the selection function 1321, a pulse sequence less susceptible to motion artifact than the pulse sequence currently used as a re-collection pulse sequence, according to the sequence selection order.

In the example of FIG. 6, instead of the FSE that requires a subject P to remain still for a long time, the next pulse sequence, namely GRASE, which is less susceptible to motion artifact compared to FSE and is capable of taking an image even if a subject P remains still only for a short time, is selected as a re-collection pulse sequence. Furthermore, if image quality does not satisfy criteria even with GRASE and motion artifact still occurs, FSE-PROPELLER is set as a re-collection pulse sequence.

However, since imaging with FSE-PROPELLER changes the contrast of the image, a user may be notified through the system control function 1311, etc. that a contrast of image has been changed.

If the cause 601 of a retake is due to banding artifact, the processing circuitry 131 may select, by the selection function 1321, a pulse sequence with a different center frequency from the current pulse sequence, and that reduces banding artifact as a next re-collection pulse sequence, according to the sequence selection order.

For example, imaging using a plurality of center frequencies to mitigate banding artifact may be performed, and SSFP with a center frequency changed from that of the initial SSFP sequence is set as a re-collection pulse sequence. Furthermore, if banding artifact occurs even with SSFP and with a changed center frequency, SSFP may be abandoned, and GRE (or fast GRE), which is a low-contrast sequence, may be set as a re-collection pulse sequence.

In a case where a predicted imaging time is exceeded because, for example, a FOV is not sufficiently large, or a retake is required due to a failure in gating, the processing circuitry 131 selects, by executing of the selection function 1321, a pulse sequence in which imaging time is shorter than that in the current pulse sequence as a re-collection pulse sequence. In other words, a re-collection sequence is set so that speed is prioritized. For example, if parallel imaging (PI) is set as an initial sequence, the combination of PI and compressed sensing (CS) may be set as a re-collection sequence.

If some part of data that needs to be retaken is usable, a differential collection sequence may be selected as a re-collection pulse sequence. For example, for a body part assumed to be less susceptible to body motion, such as a head, a differential collection sequence may be used. For a body part more prone to body motion, such as an abdomen, a differential collection sequence is not necessarily used.

If a target is not centered in an image, the couch may be moved and a re-collection pulse sequence may be performed for a retake. Alternatively, the processing circuitry 131 may select, by executing of the selection function 1321, a re-collection pulse sequence with a larger FOV than that of a pulse sequence with which imaging has failed.

The above-described image quality determination processing and re-collection pulse sequence selection processing may be performed with reference to the tables shown in FIGS. 5 and 6 as models; however, the processing may be performed with the use of a model learned based on past data. Through the performance of the image quality determination processing and the re-collection pulse sequence selection processing with the use of a trained model, it is possible to retake an imaging item with high accuracy and efficiency.

Next, a generation method for a trained model according to the present embodiment will be described with reference to FIG. 7.

Figure 7:
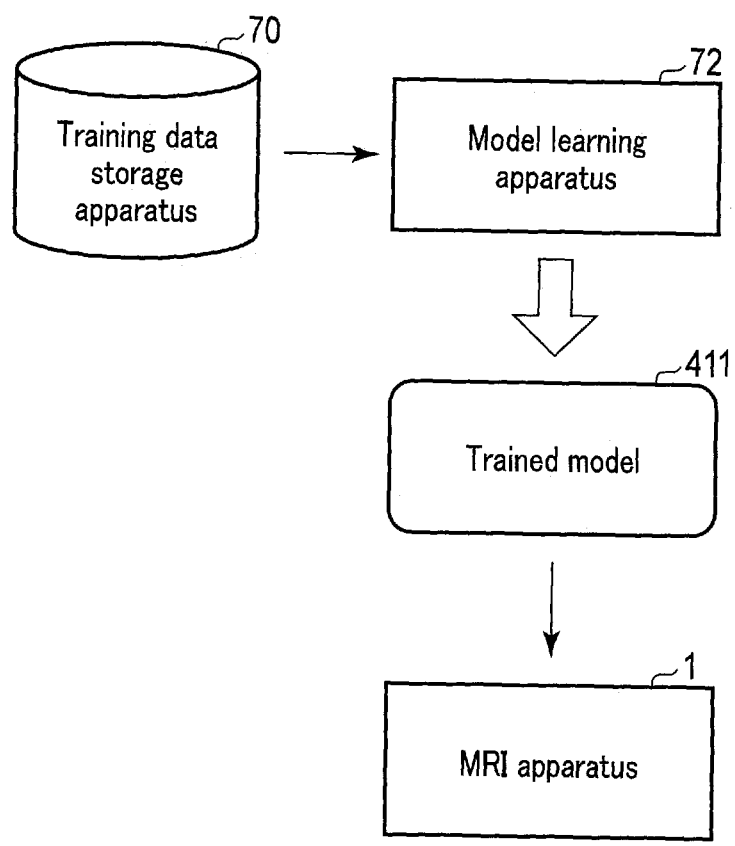
FIG. 7 is a block diagram showing an example of a learning system that generates a trained model.

FIG. 7 is a block diagram showing an example of a learning system that generates a trained model. The medical information processing system shown in FIG. 7 includes the MRI apparatus 1, a training data storage apparatus 70, and a model learning apparatus 72.

The training data storage apparatus 70 stores training data including a plurality of learning samples. For example, the training data storage apparatus 70 is a computer with large-capacity storage device. The training data storage apparatus 70 may be a large-capacity storage device communicably connected to a computer via a cable or a communication network. For such a storage device, a hard disk drive (HDD), a solid state drive (SSD), or an integrated circuit storage device, etc. can be adopted as appropriate.

The model learning apparatus 72 generates a trained model through the learning of a model by machine in accordance with a model learning program based on the training data stored in the training data storage apparatus 70. In the present embodiment, a neural network, deep learning, random forest, etc. are assumed as machine learning algorithms but not limited thereto; other machine learning algorithms may be adopted. The model learning apparatus 72 is a computer of a workstation, etc. having a processor, such as a CPU and a GPU, etc.

The model learning apparatus 72 and the training data storage apparatus 70 may be communicably connected via a cable or a communication network. The training data storage apparatus 70 may be installed in the model learning apparatus 72. In such cases, the training data may be supplied from the training data storage apparatus 70 to the model learning apparatus 72. The model learning apparatus 72 and the learning data storage apparatus 70 are not necessarily communicably connected. In this case, the training data is supplied from the training data storage apparatus 70 to the model learning apparatus 72, through a portable storage medium storing the training data thereon.

The MRI apparatus 1 and the model learning apparatus 72 may be communicably connected via a cable or a communication network. The trained model generated in the model learning apparatus 72 is supplied to the MRI apparatus 1, and the trained model is stored in the storage device 129. The MRI apparatus 1 and the model learning apparatus 72 are not necessarily communicably connected. In this case, the trained model is supplied from the model learning apparatus 72 to the MRI apparatus 1 via a portable storage medium, etc. storing the trained model thereon.

The trained model is a composite function with a parameter obtained by combining a plurality of functions. A composite function with a parameter is defined by a combination of a plurality-adjustable functions and a parameter. The trained model may be any composite function with a parameter, on the condition that it satisfies the above requests. The trained model according to the present embodiment is generated by machine-learning, a pre-machine-learned multiple-layered network (which may be simply referred to as "model") with a neural network, typically a deep neural network (DNN).

Next, the concept of the machine learning of a model by the model learning apparatus 72 will be described with reference to FIG. 8. FIG. 8 shows an example where the image quality determination processing and the re-collection pulse sequence selection processing are realized by a single trained model.

The trained model is preferably a data set consisting of input data, which in turn consist of an MR image generated based on MR data and information regarding image quality of the MR image and correct data (output data), which themselves consist of a selected pulse sequence and an imaging condition. However, in a case where an MR image generated from actually-obtained MR data cannot be acquired from the perspective of personal information protection, the model learning apparatus 72 is caused to train a model, such as a multi-layered network, through the use of training data consisting of input data (a pulse sequence and an imaging condition used for imaging and information of image quality) and correct data (a selected pulse sequence and an imaging condition), as shown in FIG. 8.

The information regarding image quality is an evaluation value of image quality, for example, and may be a standard deviation (SD) value of an image, or an evaluation value of the MR image by a user, such as a technician or radiologist.

Ideally, actions at the time of a past retake performed at a hospital should be learned. In other words, if image quality of an MR image is poor, a result of selecting a pulse sequence is trained; for example, information relating to the kind of pulse sequence to which the failed pulse sequence is switched in order to perform a retake.

Even if the same pulse sequence is used, a result of selecting an imaging condition, for example a retake under an imaging condition that deteriorates image quality more in the z-axis direction than in the y-axis direction, may be trained. In other words, as long as the imaging conditions are different, the different MR data are collected even if the pulse sequence of the input data and the selected pulse sequence, which serves as correct data, are the same; accordingly, such a model should be learned as training data.

When a trained model is trained, the model learning apparatus 72 is caused to train a multi-layered network, which is a model for learning, with the use of the above-described training data, at the time of shipping a product, for example. The trained model is installed in the processing circuitry 131 or the storage device 129 of the MRI apparatus 1. It may be possible to update the trained model at the time of repair or software update.

The model data may be generated so as to include a selection method for pulse sequence that has been performed at a plurality of hospitals. Through training of a selection method for pulse sequences performed in a plurality of hospitals, it is possible to average the tendency in the selection of a re-collection pulse sequence and obtain versatile data.

Next, the concept of the use of the model learned through machine learning as shown in FIG. 8 will be described with reference to FIG. 9.

When a trained model is used, the MR image quality determination processing and the re-collection pulse sequence selection processing are performed by the trained model into which obtained MR data, an imaging condition, time relating to an examination are input, and if a retake is necessary, a re-collection pulse sequence and an imaging condition are output. A time relating to an examination is, for example, a remaining time of a permitted examination time, or a set of a permitted examination time and a time elapsed since an examination has begun.

If an original pulse sequence that requires a retake due to unsatisfactory image quality is compared with other pulse sequence candidates, the processing circuitry 131 may select, by executing of the selection function 1321, the same pulse sequence as the original sequence in which an imaging condition has been changed, as a re-collection pulse sequence.

FIGS. 8 and 9 show an example of performance of the image quality determination processing and the re-collection pulse sequence selection processing by a single trained model; however, different trained models may perform the determination and the selection.

A concept of machine learning of a model by the model learning apparatus 72, with the image quality determination processing and the re-collection pulse sequence selection processing by different trained models, will be described with reference to FIG. 10.

In the model learning for the image quality determination processing, the model learning apparatus 72 trains a first model, such as a multi-layered network, with the use of training data consisting of the MR data as input data and a determination result as correct data.

In the model learning for the re-collection pulse sequence selection processing, the model learning apparatus 72 learns a second model, such as a multi-layered network, with the use of training data consisting of a determination result, a pulse sequence, and an imaging condition as input data and a selected pulse sequence as correct data.

Figure 11:
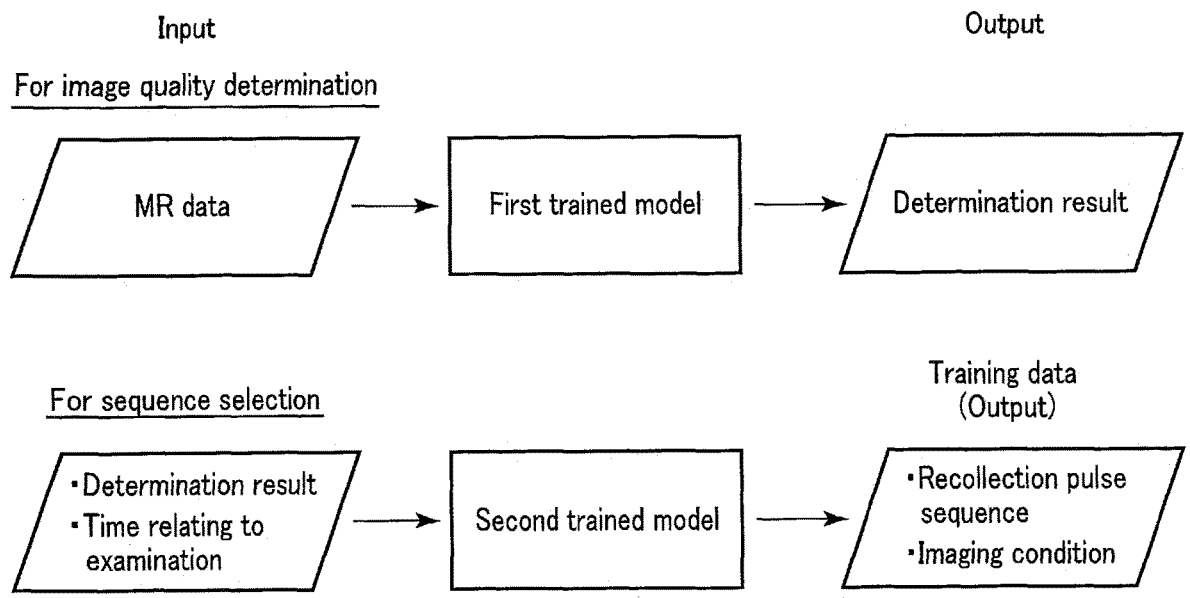
FIG. 11 is a conceptual drawing of a use of the trained model according to FIG. 10.

Next, the use of the trained model generated as shown in FIG. 10 will be described with reference to FIG. 11.

When the trained model for the image quality processing is used, obtained MR data is input into a first trained model, so that the image quality determination processing is performed by the first trained model, and a determination result is output.

In the model training for the re-collection pulse sequence selection processing, the result of determination output from the first trained model and a time relating to examination are input to a second trained model, the re-collection pulse sequence selection processing is performed by the second trained model, and a re-collection pulse sequence and an imaging condition are output.

A determination result for the image quality input to the second trained model is not limited to the determination result output from the first trained model; it may be a determination result obtained through the realization of the above-described image quality determination processing by a conventional method.

There may be a case where imaging corresponding to a next imaging item is performed without the performance of imaging corresponding to a current imaging item that requires a retake, in order to balance a desired image quality level with an elapsed examination time, or a case where an MR image that achieves desired image quality cannot be obtained depending on a reselected re-collection pulse sequence. In this case, the system control function 1311 may add a text indicating that an MR image cannot be taken, or that an MR image that does not achieve desired image quality will be generated as additional information to the MR image. Such texts may be output to the display 127.

Furthermore, in addition to, or instead of, the additional information, if an examination situation in an examination room can be ascertained, a message requesting a user to obtain more examination time may be presented to the user. Specifically, the processing circuitry 131 may obtain a vacancy status of the examination room from a hospital intra network (not shown), and if there is a vacant room available immediately after the current examination time, a message may be displayed in this regard.

There may be a case where there is a lack of training data when a trained model is generated. Accordingly, an imaging list in which a default re-collection pulse sequence order is set may be used. It is thereby possible to use a default pulse sequence as fallback.

If the processing in step S205, S208, and S209 shown in FIG. 2 is repeated, in the image quality determination processing in step S205, a plurality of criteria (thresholds) are set, and every time a re-collection pulse sequence is selected, the selection of other pulse sequences through lowering criteria for image quality is permitted.

Figure 12:
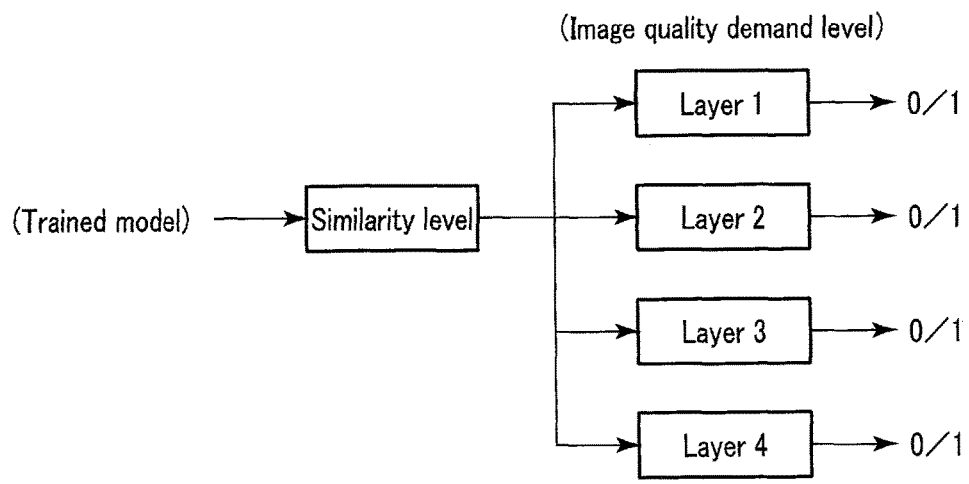
FIG. 12 is a drawing showing an example of image quality determination when a similarity level is output from a trained model.

An example of the image quality determination processing by a trained model with the use of a plurality of criteria will be described with reference to FIG. 12.

That which is output from a trained model is a similarity level. An output of a similarity level is input into a plurality layers (layer 1 through layer 4 in the present embodiment) in accordance with an image quality demand level. In each layer, if the similarity level is higher than the image quality demand level, "1" is output, and if the similarity level is lower than the image quality demand level, "0" is output. Suppose the demanded image quality is set to be higher from layer 1 toward layer 4. For example, in an initial sequence, it is determined that a retake is performed if the image quality demand level at layer 4 is not satisfied.

In a re-collection pulse sequence, a retake is determined to be successful as long as the image quality demand level is satisfied up to layer 3, and there is no need to satisfy the level at layer 4, and if the level at layer 3 is not satisfied, a retake with the use of a different re-collection pulse sequence is determined.

From the viewpoint of workflow, the processing shown in the flow chart of FIG. 2 is controlled in such a manner that the processing is automatically performed by a user's instruction to cause the MRI apparatus 1 to start imaging (for example, by pressing a start button). The processing circuitry 131 may switch between automatic performance of, by executing of the system control function 1311, the re-collection pulse sequence selection processing, setting of an imaging condition, and collection of MR data in accordance with a re-collection pulse sequence, and automatic performance of the selection processing and the setting of an imaging condition and the manual changing, if necessary, of the imaging condition when imaging is actually performed.

According to the above-described embodiment, if image quality of an image based on obtained MR data does not satisfy the criteria, a simple retake is not performed; rather, a re-collection pulse sequence is selected instead of a pulse sequence with which imaging fails. By performing at least the re-collection pulse sequence selection in accordance with a trained model, it is possible to obtain an MR image automatically and with consistent quality by an MRI apparatus, with reduced dependence on technicians and, furthermore, a reduced burden on technicians.

Moreover, the functions described in connection with the above embodiment may be implemented, for example, by installing a program for executing the processing in a computer, such as a workstation, etc., and expanding the program in a memory. The program that causes the computer to execute the processing can be stored and distributed by means of a storage medium, such as a magnetic disk (a hard disk, etc.), an optical disk (CD-ROM, DVD, etc.), and a semiconductor memory.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising circuitry configured to:
   collect magnetic resonance data for imaging in accordance with a pulse sequence;
   determine image quality based on the magnetic resonance data; and
   select a re-collection pulse sequence when it is determined that the image quality does not satisfy criteria, the re-collection pulse sequence having at least one of a type of sequence or an imaging condition differing from that of the pulse sequence.

2. The apparatus according to claim 1, wherein
   the processing circuitry determines the re-collection pulse sequence that allows collection within a permitted time, and
   the processing circuitry re-collects magnetic resonance data in accordance with the selected re-collection pulse sequence.

3. The apparatus according to claim 1, wherein
   the processing circuitry determines the re-collection pulse sequence from magnetic resonance data targeted for processing in accordance with a model into which a time relating to an examination and magnetic resonance data are input, and from which a re-collection pulse sequence is output.

4. The apparatus according to claim 1, wherein
   the processing circuitry generates a result of image quality determination from magnetic resonance image targeted for processing in accordance with a first model into which magnetic resonance data is input, and from which a result of determining image quality is output.

5. The apparatus according to claim 1, wherein
   the processing circuitry determines a re-collection pulse sequence from a result of image quality determination in accordance with a second model into which a result of image quality determination and a remainder of a permitted examination time are input, and from which a re-collection pulse sequence is output.

6. The apparatus according to claim 1, wherein
   imaging relating to an emphasis method for image contrast is associated with a plurality of pulse sequence candidates, and
   the pulse sequence and the re-collection pulse sequence are selected from the plurality of pulse sequence candidates.

7. The apparatus according to claim 6, wherein
   the magnetic resonance data is collected in accordance with an imaging list including a plurality of imaging items, and
   when a retake is required, the processing circuitry reselects, from the plurality of pulse sequence candidates, a pulse sequence relating to a yet-to-be-acquired imaging item included in the imaging list based on a remainder of a permitted examination time.

8. The apparatus according to claim 6, wherein
   the processing circuitry selects another re-collection pulse sequence based on an imaging time assumed for other imaging items and a remainder of a permitted examination time when image quality determined based on magnetic resonance data collected in accordance with the re-collection pulse sequence does not satisfy criteria.

9. The resonance imaging apparatus according to claim 1, wherein
   the re-collection pulse sequence has a shorter imaging time than an imaging time of the pulse sequence.

10. The apparatus according to claim 1, wherein
    the re-collection pulse sequence receives less influence from motion artifact than the pulse sequence.

11. The apparatus according to claim 1, wherein
    the re-collection pulse sequence uses a center frequency different from a center frequency of the pulse sequence.

12. The apparatus according to claim 1, wherein
    the re-collection pulse sequence is performed along an operation of movement of a couch.

13. The apparatus according to claim 1, wherein
    the re-collection pulse sequence has a larger field of view than a field of view of the pulse sequence.

14. The apparatus according to claim 1, wherein
    the pulse sequence and the re-collection pulse sequence include collection of a calibration signal for determining the image quality.

15. The apparatus according to claim 14, wherein
    the calibration signal is an echo signal immediately after an application of an excitation pulse or a prepulse, or an echo signal immediately before an application of an excitation pulse or a prepulse.

16. The apparatus according to claim 1, wherein
    the processing circuitry selects, as a re-collection pulse sequence, a pulse sequence for retaking a correction map relating to correction of a magnetic field.

17. The apparatus according to claim 1, wherein
    the processing circuitry further configured to control switching between i) automatic performance of a re-collection pulse sequence selection processing, an imaging condition setting processing, and a magnetic resonance data collection processing in accordance with the re-collection pulse sequence, and ii) automatic performance of the re-collection pulse sequence selection processing and the imaging condition setting processing and manual changing of the imaging condition in advance of performing the collection processing.

18. The apparatus according to claim 1, wherein
    the processing circuitry is further configured to generate a report relating to a result of examination after collection of the magnetic resonance imaging.

* * * * *